United States Patent [19]

Farcot

[11] Patent Number: 5,421,825
[45] Date of Patent: Jun. 6, 1995

[54] PERCUTANEOUS VASCULAR INTRODUCTION DEVICE FOR THE FEEDING OF AN EXTRACORPOREAL BLOOD CIRCUIT

[76] Inventor: Jean-Christian Farcot, 20 rue Parmentier, 92200 Neuilly Sur Seine, France

[21] Appl. No.: 132,302

[22] Filed: Oct. 6, 1993

[51] Int. Cl.$^6$ .......................................... A61M 25/00
[52] U.S. Cl. ..................................... 604/44; 604/169; 604/284
[58] Field of Search ........................... 604/4-6, 604/43, 44, 164, 167, 169, 264, 284

[56] References Cited

U.S. PATENT DOCUMENTS

| | | | |
|---|---|---|---|
| 2,832,341 | 4/1958 | Stack | 604/43 |
| 4,037,599 | 7/1977 | Raulerson | 604/4 |
| 4,202,232 | 5/1980 | Tersteegen et al. | 604/164 |
| 4,270,535 | 6/1981 | Bogue et al. | 604/164 |
| 4,493,708 | 1/1985 | Sugisawa | 604/44 |
| 4,531,935 | 7/1985 | Berryessa | 604/44 |
| 4,722,725 | 2/1988 | Sawyer et al. | 604/167 |
| 4,842,582 | 6/1989 | Mahurkar | 604/280 |
| 4,897,079 | 1/1990 | Zaleski et al. | 604/43 |
| 4,959,058 | 9/1990 | Michelson | |
| 5,053,004 | 10/1991 | Markel et al. | 604/43 |
| 5,106,363 | 4/1992 | Nobuyoshi | 604/280 |

FOREIGN PATENT DOCUMENTS

| | | |
|---|---|---|
| 0000831 | 2/1979 | European Pat. Off. . |
| 0365048 | 4/1990 | European Pat. Off. . |
| 515119 | 11/1992 | European Pat. Off. ............ 604/280 |
| 2024791 | 12/1971 | Germany . |
| 3006291 | 8/1980 | Germany . |
| 2017499 | 10/1979 | United Kingdom . |
| 286145 | 11/1970 | U.S.S.R. ............................... 604/43 |

*Primary Examiner*—Peter A. Aschenbrenner
*Assistant Examiner*—Nancy Mulcare
*Attorney, Agent, or Firm*—Young & Thompson

[57] ABSTRACT

The vascular introduction device is of the lateral arm type. It comprises a tubular body defining an introduction channel enabling, after installation of the distal part of the introduction device in a blood vessel of a patient to be treated, the introduction of a catheter into the vascular system up to where the operation is be performed. The introduction device is provided over part of its length with a longitudinal bulge whose inner wall defines a cavity merged with the introduction channel and communicating directly with the lateral arm. The tubular body is provided with blood inlet orifices arranged at least in the wall defining the cavity. The lateral arm thus enables feeding of a closed external blood circuit comprising a perfusion pump, with a sufficient blood rate in terms of pressure and flow, equal to the rate that would be obtained by a contralateral puncture point. The blood thus sampled off can be reinjected into the patient via the dilatation catheter. This vascular introduction device is mainly destined for use in a radiological or heart surgery operation.

7 Claims, 2 Drawing Sheets

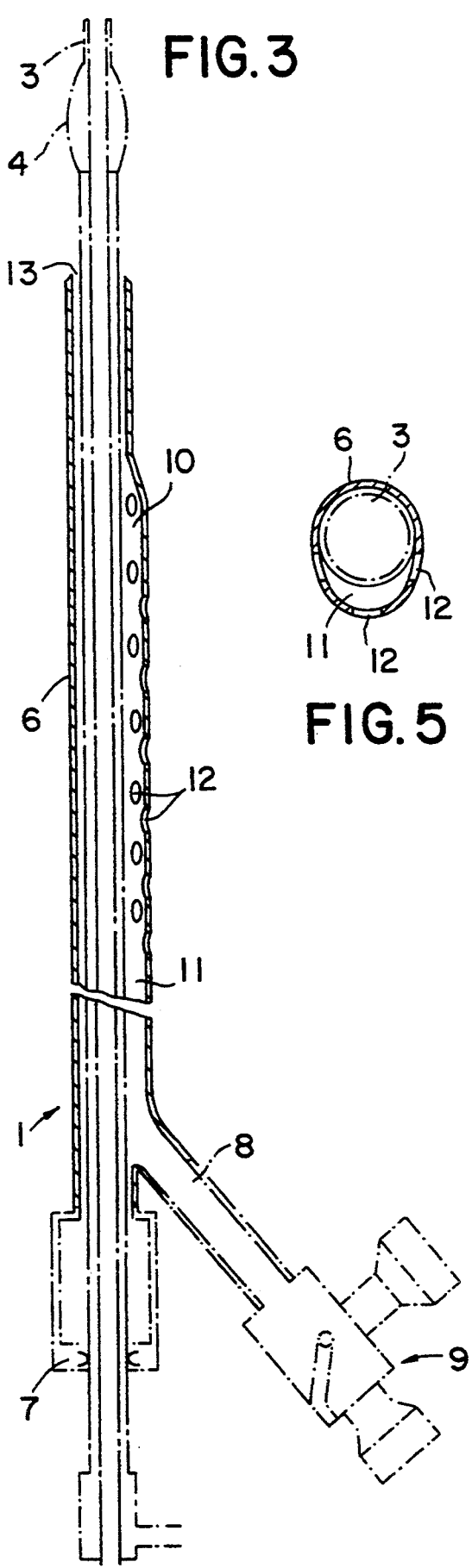
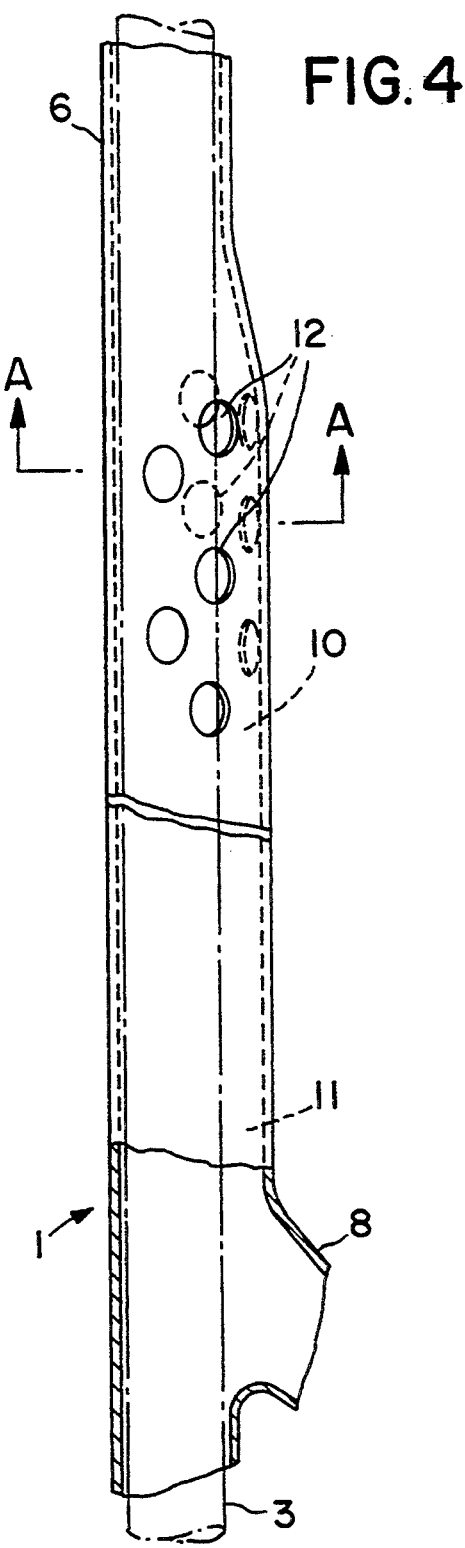

PERCUTANEOUS VASCULAR INTRODUCTION DEVICE FOR THE FEEDING OF AN EXTRACORPOREAL BLOOD CIRCUIT

BACKGROUND OF THE INVENTION

1. Field of the Invention

This invention relates to a vascular introduction device with a lateral arm, this introduction device being destined to be used to insert a catheter into the vascular system.

The introduction device proper is in the shape of a tube which is provided with a non-return valve at its rear or proximal part. The introduction device is, prior to being installed in the blood vessel, slid onto a pointed cylindrical rod disposed so as to protrude from the opposite ends of the introduction device.

This cylindrical rod is exclusively used at the time of installing the introduction device in the blood vessel subsequent to the opening of a hole in the skin of the patient to be treated, which is performed by means of a needle.

The cylindrical rod is relatively rigid and serves to elastically enlarge the passage towards the vessel as it progresses into the latter. The rod thus facilitates the introduction of the introduction device which follows immediately after, thereby producing a successive increase in the diameter of the entire part inserted into the vessel. The rod is then extracted and replaced by a catheter.

To simplify the utilization of the different types of catheterization, a measurement further applied using diameter measurement units F (French) and the introduction devices currently used for coronary or vascular angiometrics generally have a diameter of 8 F. In such an introduction device, a 7 F catheter can be inserted.

The size of the hole and of the passage dilated by the introduction of the introduction device must be as restricted as possible in order to limit bleeding once this operation has been completed and the introduction device removed, this being all the more delicate that the patient has always, prior to the operation, received anticoagulants intended to reduce the risk of thrombosis formation.

The lateral arm of the introduction device, which is usually terminated by a tap with plural channels, further enables the performing of local rinsing by injection of a fluid, thereby neutralizing clots. This arm can also be connected to a force pump to inject drugs into the vessel or to sample off small quantities of blood by aspiration.

The catheter inserted into the vascular system by means of such an introduction device can be e.g. used to take pressure measurement readings in the different cavities of the heart and to appraise the different functionings of the myocardium and valves.

The introduction device according to the invention can be advantageously used to perform an angioplasty in a coronary artery or peripheral artery. This operation is performed by means of a catheter which is provided, at its distal end, with a dilatation bulb that can be inflated to compress atheromatous plates.

2. Description of the Prior Art

Such catheters are disclosed in detail in French patent No. 2,638,364 of the same applicant, this patent corresponding to U.S. patent application No.291,307, now U.S. Pat. No. 5,057,120.

One of the problems associated angioplasty is that, throughout the period of inflation of the dilatation bulb, the blood flow completely interrupted within t he corresponding artery. It is for this reason that techniques have been developed enabling the time of inflation of dilatation bulbs to be increased. To this end, it has thus been proposed to perform blood perfusion beyond the dilatation bulb by using the catheter itself as a perfusion tube.

Throughout this operation, blood is thus forced back, in synchronism with the heart rate of the patient, in the central channel of the catheter to ensure perfusion downstream of this dilatation bulb in order to avoid various undesirable and dangerous phenomena such as electrical modifications, thoracic pain, left ventricular contractility anomalies.

In order to perform such a perfusion, it has hitherto been necessary to make a second hole towards an artery into which a second introduction device is inserted, though this time only to sample off blood which is then reinjected into the patient via the catheter. An external circuit was thus created comprising a pulsatile unit serving as a perfusion pump and which is capable of aspirating the blood coming from the second introduction device, and of forcing it back periodically towards the catheter according to a variable flow rate corresponding to the diastole and systole phases of the patient's heartbeat.

It is obvious that the need to make a second hole to sample off a quantity of blood corresponding to approximately 100 ml/minute is a major drawback that can prove dangerous when one considers that the operation is often performed on a patient already seriously ill.

OBJECT OF THE INVENTION

The main object of this invention is to attenuate this risk by providing a vascular introduction device enabling a single hole to be made in order to perform an operation such as an angioplasty and to simultaneously sample off the required quantity of blood by this same introduction device, without aspiration.

SUMMARY OF THE INVENTION

Accordingly, the object of the invention is an arterial vascular introduction device of the type comprising a lateral arm fitted with a non-return valve disposed at its proximal end and with blood inlet orifices at its distal end, and comprising a tubular body defining an introduction channel enabling, after installation of the distal part of the introduction device in a blood vessel of a patient to be treated, the introduction of a catheter in to the vascular system up to where the operation is to be performed by catheterization, wherein the device is provided over part of its length with a longitudinal bulge whose inner wall defines a cavity merged with the introduction channel and communicating directly with the lateral arm, the cross section of the introduction device at the site of the bulge has an ovoid shape, and the device is provided with blood inlet orifices arranged at least in the wall of the longitudinal bulge defining the cavity.

By way of the means provided by the invention, it is thus possible to sample off, directly by a single introduction device, the quantity of blood required to feed an extracorporeal blood circuit while a prolonged angioplasty is being performed.

According to further features of the invention:

blood inlet orifices are regularly disposed all around the introduction device over a length corresponding to a distal zone of the cavity;

the orifices are distributed over approximately one-third of the length of the introduction device;

the sum of the areas of the orifices is equal to or greater than the area of the distal opening of the introduction device;

the lateral arm is integral with the tubular body of the introduction device;

the lateral arm is inclined towards the rear;

the lateral arm forms an angle of approximately 30° with the axis of the introduction device;

the cross-sectional area of the cavity provides an increase of the cross-sectional area at the bulge of the order of magnitude of approximately 0.5 French;

the number of orifices ranges from 5 to 10.

BRIEF DESCRIPTION OF THE DRAWINGS

Further features and advantages of the invention will be apparent from the following particular description of several preferred embodiments of this invention as illustrated in the corresponding accompanying drawings in which:

FIG. 3 is a schematic longitudinal sectional view of an introduction device according to the invention run through by a dilatation bulb catheter;

FIG. 4 shows, on a larger scale, a partial longitudinal section of a part of the introduction device in FIG. 3;

FIG. 5 is a cross-sectional view A—A of the introduction device in FIG. 4.

DESCRIPTION OF THE PREFERRED EMBODIMENTS

Figure 1:
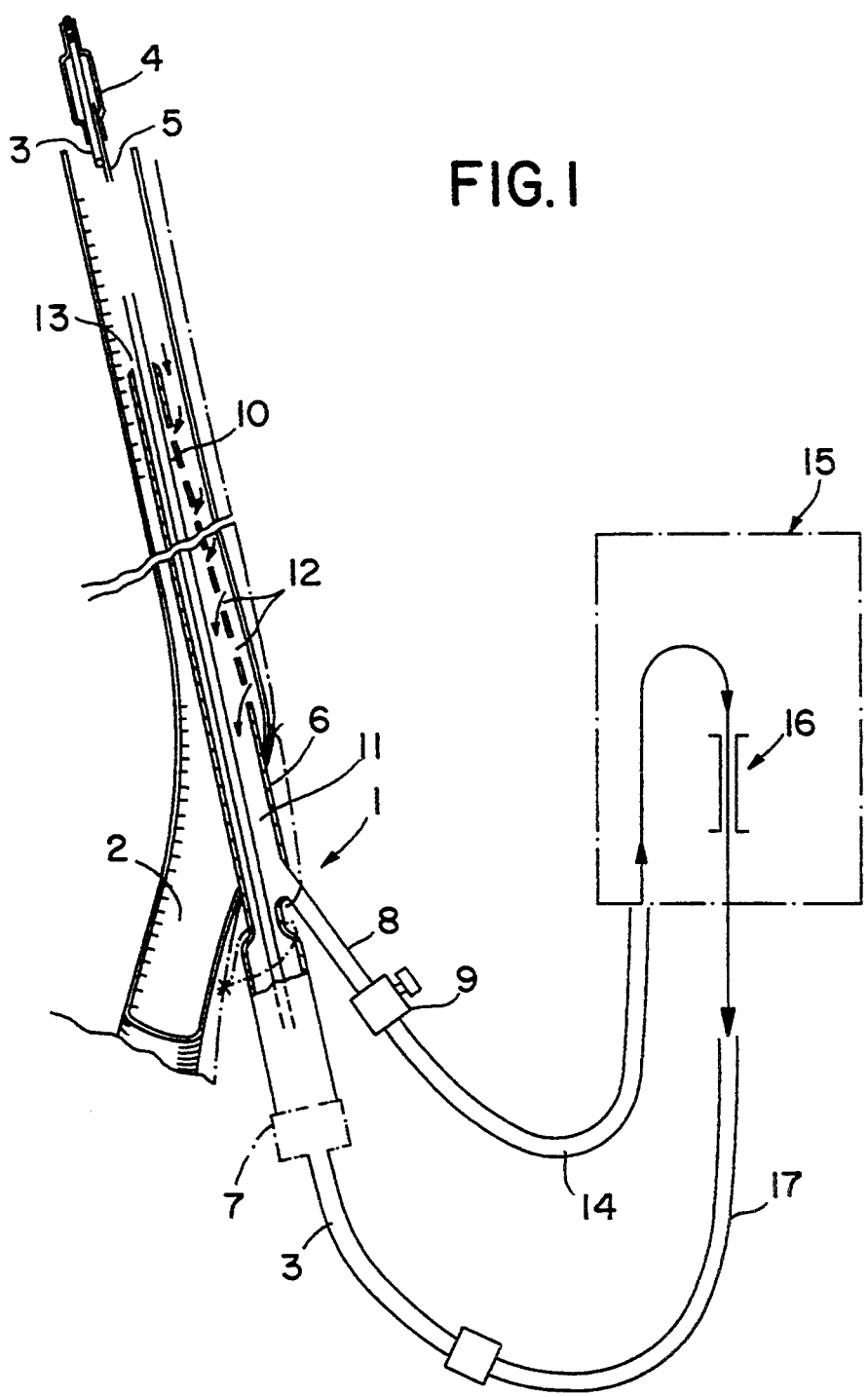
FIG. 1 is a schematic overall view showing an introduction device according to the invention in position in an artery and connected to a perfusion pump by a closed external circuit.

FIG. 1 schematically shows an introduction device 1 according to the invention after installation thereof in a peripheral artery 2, usually a common iliac artery.

In the example illustrated in this figure, the introduction device is used to insert a catheter 3 for angioplasty into the vascular system. The clearance between the inner wall of the introduction device 1 and the outer wall of the catheter 3 is as small as possible while enabling the catheter to advance through the introduction device without difficulty. This problem is however already solved thanks to the diameter measurement system in French (F).

Figure 2:
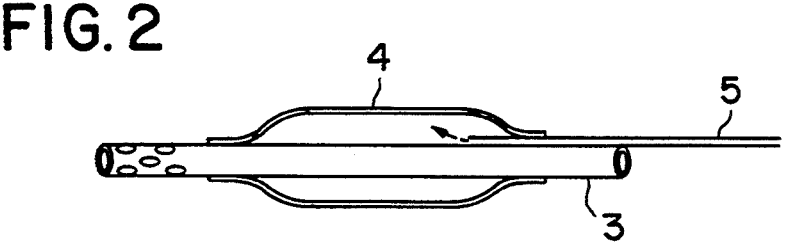
FIG. 2 shows, on a larger scale, the end of a dilatation bulb catheter used for an angioplasty.

The catheter 3 is, at its distal end, provided with a dilatation bulb 4 (see FIG. 2) or any other system used in heart surgery. This dilatation bulb is displaced with the catheter 3 towards the place where the angioplasty is to be performed, e.g. in a coronary artery. The dilatation bulb 4 is connected to an inflation duct 5 fixed to or part of the catheter 3. This dilatation bulb can thus be inflated in order to compress atheromatous plates formed on the inner wall of the vessel to be treated.

The introduction device 1 is formed by a tubular body 6 whose inner wall defines a channel for introduction of the catheter. The tubular body 6 is, at its proximal end, provided with a non-return valve 7 preventing the projection of blood towards the exterior in the absence of the catheter 3 in the internal channel of the tubular body.

The tubular body 6 is connected to a lateral arm 8, which is equipped with a multichannel valve 9 at its free extremity. The lateral arm is preferably integral with the tubular body 6.

The lateral arm 8 communicates directly with a longitudinal bulge 10 of the wall of the tubular body 6. This bulge extends parallel to the axis of the tubular body over approximately one-third of the length of the latter.

FIG. 5 shows a cross-section at the location of the bulge 10 (see A—A in FIG. 4). This section preferably comprises an ovoid shape and if, by way of example, the introduction device is an 8 F device, the cross-sectional area increased by the presence of the bulge 10 corresponds to a tubular body of approximately 8.5 F to 9 F, i.e. an increase of approximately 0.5 F to 1.0 F, which is a virtually negligible increase in this given application.

The inner wall of the bulge 10 thus defines a cavity 11 merged with the introduction channel formed in the tubular body 6 of the introduction device. This cavity 11 is, in a distal zone of its wall, provided with blood inlet orifices 12. Thanks to the blood pressure which normally varies between 130 mm Hg and 70 mm Hg, blood in the artery is driven inside the cavity 11 where it enters through these orifices 12.

For indicative purposes, these orifices are 5 to 10 in number. This number must not be too high so as not to unduly weaken the rigidity of the wall of the introduction device.

The orifices 12 can advantageously disposed all around the introduction device over a length corresponding to the distal zone of the cavity.

In this way, close to the part of the wall opposite that of the cavity 11, the catheter finds itself, due to the effects of the arterial blood pressure, slightly pushed back into the cavity so that blood can easily enter by the corresponding holes, flow around the catheter and reach the cavity 11 before exiting via the lateral arm 8.

The sum of the areas of the orifices 12 is preferably equal to at least the area of the distal opening of introduction device 1.

In order to facilitate the exiting of the blood via the lateral arm 8, the latter is advantageously inclined towards the rear. The lateral arm can thus form an angle of approximately 30° with the axis of the introduction device.

FIG. 1 shows, in an overall view, that the lateral arm 8 of the introduction device is connected by means of a first tube 14 to a closed external blood circuit comprising a pulsatile unit 15 which, by means of a perfusion pump 16, returns the blood towards the interior of the catheter 3 via second tube 17. The blood is then ejected beyond the dilatation bulb 4 of the catheter.

Moreover, experiments have shown that the blood leaves via the lateral arm without practically any pressure loss in relation to the arterial pressure.

According to the invention, it is thus possible to directly sample off, by a single introduction device, the quantity of blood required to perform a prolonged angioplasty. It can also be used e.g. to monitor exact measurements of arterial pressure or of biological parameters, and to take blood samples.

Furthermore, it is evident that the lateral arm 8 can be further used in a conventional manner for the injection of drugs, etc.

I claim:

1. An arterial vascular introduction device for the introduction of a catheter into a patient's vascular system comprising:

an elongated tubular body having open proximal and distal ends, said elongated tubular body having an inner wall defining a catheter introduction channel extending between said open proximal end and said open distal end;

a lateral arm integral with the tubular body between the tubular body proximal and distal ends at a position proximate said proximal end, said lateral arm having a lumen therethrough in fluid communication with said catheter introduction channel;

a non-return valve positioned at the open proximal end of said elongated tubular body for permitting the introduction of a catheter therethrough and for preventing the flow of blood from the tubular body proximal end before introduction of the catheter, wherein the wall of the elongated tubular body further comprises a longitudinal bulge extending parallel to a longitudinal axis of the tubular body; said wall exhibiting in a cross section through the bulge an ovoid shape and defining inside the bulge a longitudinal cavity merged along the length of the longitudinal bulge with the catheter introduction channel and communicating directly with the lumen of the lateral arm, and blood inlet orifices being arranged in said cavity, wherein the sum of the areas of the orifices is at least equal to the area of a distal end opening of said introduction device so as to permit, when the catheter extends through the entire length of the device and occupies the catheter introduction channel, a simultaneous exiting of a required quantity of blood for feeding, without aspiration, an extracorporeal blood circuit.

2. The introduction device as claimed in claim 1, wherein the blood inlet orifices are regularly disposed all around the introduction device over a length corresponding to a distal zone of the cavity.

3. The introduction device as claimed in claim 1, wherein the orifices are distributed over approximately one-third of the length of said introduction device.

4. The introduction device as claimed in claim 1, wherein the lateral arm is inclined downwardly with respect to said longitudinal axis.

5. The introduction device as claimed in claim 4, wherein the lateral arm forms an angle of approximately 30° with said longitudinal axis.

6. The introduction device as claimed in claim 1, wherein the cross-sectional area of the cavity provides an increase of the cross-sectional area of the bulge of the order of magnitude of approximately 0.5 to 1.0 French.

7. The introduction device as claimed in claim 1, wherein the number of orifices ranges from 5 to 10.

* * * * *